United States Patent [19]
Miller et al.

[11] Patent Number: 5,833,864
[45] Date of Patent: *Nov. 10, 1998

[54] METHOD FOR THE REDUCTION AND CONTROL OF THE RELEASE OF GAS AND ODORS FROM SEWAGE AND WASTE WATER

[75] Inventors: Thomas M. Miller, Walnut, Calif.; Mark A. Shand, Findlay, Ohio

[73] Assignee: PSC Technologies, Inc., King of Prussia, Pa.

[*] Notice: This patent issued on a continued prosecution application filed under 37 CFR 1.53(d), and is subject to the twenty year patent term provisions of 35 U.S.C. 154(a)(2).

[21] Appl. No.: 680,502

[22] Filed: Jul. 8, 1996

Related U.S. Application Data

[63] Continuation of Ser. No. 386,735, Feb. 10, 1995, abandoned.
[51] Int. Cl.$^6$ ................................ C02F 1/66; C02F 11/00
[52] U.S. Cl. .......................... 210/724; 210/749; 210/916; 210/903
[58] Field of Search ..................... 210/724, 749, 210/916, 903

[56] References Cited

U.S. PATENT DOCUMENTS

| | | | |
|---|---|---|---|
| 2,852,584 | 9/1958 | Komline | 210/916 |
| 3,080,253 | 3/1963 | Dietz et al. . | |
| 3,377,271 | 4/1968 | Cann | 210/45 |
| 3,697,322 | 10/1972 | Lee et al. . | |
| 3,705,098 | 12/1972 | Shepherd et al. | 210/63 |
| 3,862,851 | 1/1975 | Speirs et al. . | |
| 3,974,783 | 8/1976 | Flynn | 110/8 |
| 4,118,319 | 10/1978 | Miyanohara et al. | 210/51 |
| 4,125,466 | 11/1978 | Miyanohara et al. | 210/67 |
| 4,169,906 | 10/1979 | Hallstrom et al. . | |
| 4,456,635 | 6/1984 | Albanese et al. . | |
| 4,615,918 | 10/1986 | Reichert et al. . | |
| 4,668,541 | 5/1987 | Fagerlund . | |
| 4,670,315 | 6/1987 | Hillemeier et al. . | |
| 4,675,114 | 6/1987 | Zagyvai et al. | 210/666 |
| 4,710,404 | 12/1987 | Reichert et al. . | |
| 4,786,525 | 11/1988 | Kayser et al. . | |
| 5,228,995 | 7/1993 | Stover | 210/917 |
| 5,246,641 | 9/1993 | Perkins et al. . | |
| 5,422,015 | 6/1995 | Angell | 210/751 |

FOREIGN PATENT DOCUMENTS

| | | |
|---|---|---|
| 1326682 | 4/1963 | France . |
| 424919 | 3/1935 | United Kingdom . |
| 2123516 | 2/1984 | United Kingdom . |

OTHER PUBLICATIONS

Excerpts from ASCE Manuals and Reports on Engineering Practice—No. 69 titled "Sulfide in Wastewater Collection and Treatment Systems".

Davis Process Division of Davis Water & Waste Industries, Inc.; Process Division Technical Bulletin No. B–401, Bioxide . . . the natural solution, A Proprietary Product Designed to Promote Naturally Occurring Process Within Wastewater Collection and Treatment Systems Which Eliminate Order Producing Compounds.

Sewer Corrosion Control and Rehabilitation, County Sanitation Districts of Los Angeles County, 5 Pages.

Caustic Spray For Sewer Crown Corrosion Control, by Jamie Baida, 11 Pages.

Microbial Energy Generation/Oxidation of Inorganic Substrates, pp. 158–159.

Preparing Collection Systems for Water Conservation, pp. 52–57, Water Environment & Technology, Aug. 1993.

(List continued on next page.)

*Primary Examiner*—Neil McCarthy
*Attorney, Agent, or Firm*—Ostrolenk, Faber, Gerb & Soffen, LLP

[57] ABSTRACT

A method for reducing and controlling the formation and release of acid gases and odors associated therewith, particularly from hydrogen sulfide, in sewerage or waste water, wherein magnesium hydroxide and/or magnesium oxide are added to the sewerage or waste water.

26 Claims, 3 Drawing Sheets

OTHER PUBLICATIONS

Metals Meet Their Match, pp. 69–73, Water Environment & Technology, Sep. 1993.

Product Report/Surfactants for household detergents—petrochemical raw materials and uses, pp. 40–41 & 46, C&EN, Jan. 24, 1994.

Generation and Control Sulfide in Filled Pipes, by Dr. Richard D. Pomeroy, Pomeroy and Associates, Pasadena, Calif., From Sewage and Industrial Wastes, vol. 31, No. 9, 1959.

Process Design Manual for Sulfide Control in Sanitary Sewerage Systems, U.S. Environmental Protection Agency Technology Transfer, Oct. 1974, 9 Pages.

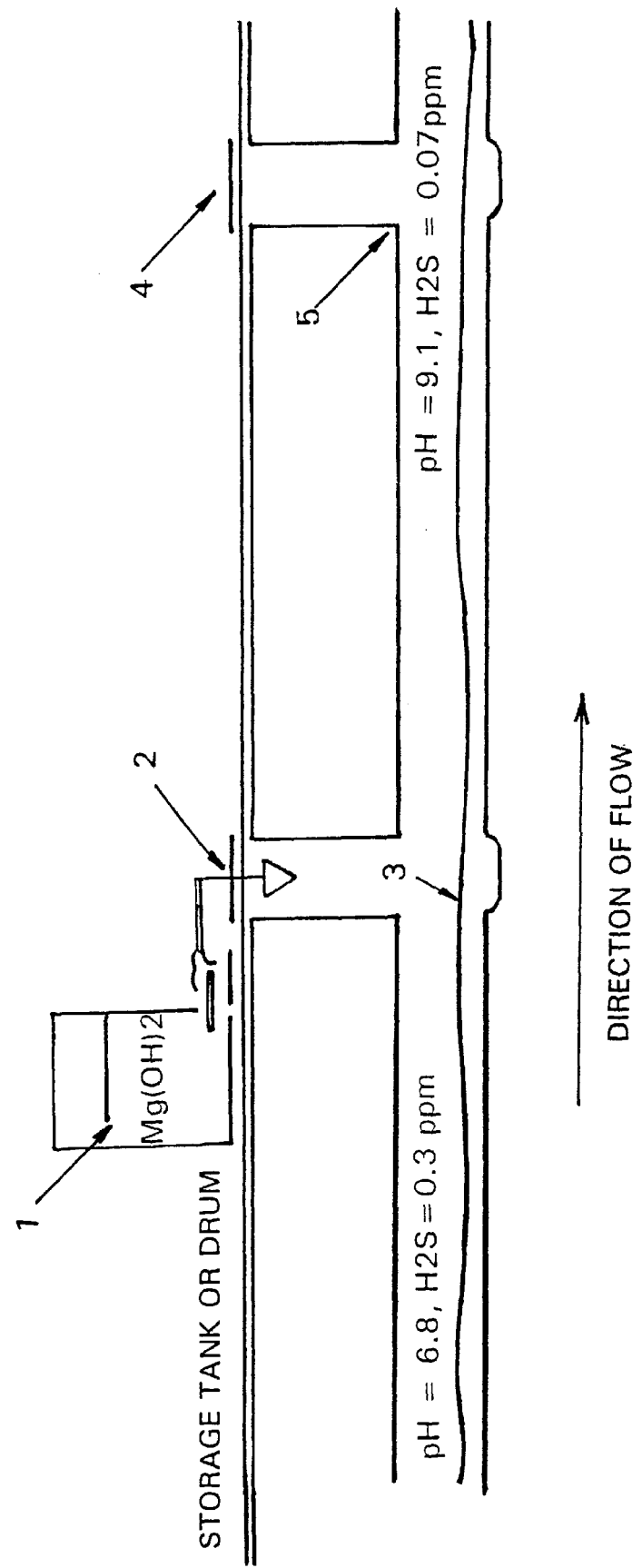

METHOD FOR THE REDUCTION AND CONTROL OF THE RELEASE OF GAS AND ODORS FROM SEWAGE AND WASTE WATER

CROSS-REFERENCE TO RELATED APPLICATIONS

This application is a continuing application of U.S. Ser. No. 08/386,735 filed Feb. 10, 1995 now abandoned.

BACKGROUND OF THE INVENTION

1. Field of the Invention

The present invention relates to the control of gaseous release and of odors associated with sewerage and waste water and more particularly, to the reduction and control of the release of acid gases, such as hydrogen sulfide, from sewerage or waste water.

2. Description of the Related Art

Sewerage and waste water generally contain sulfates and other contaminants which, upon reduction, become (directly or indirectly) gaseous compounds which are released generating unpleasant odors. For example, sulfates are reduced to sulfides associated with the release of hydrogen sulfide gas. The reduction of sulfates can proceed by the action of sulfate-reducing bacteria including *Desulfovibro sulfricans*. Hydrogen sulfide and other acid gases which are released include potentially dangerous contaminants and lead to unpleasant odors.

Several methods have been proposed and used to control the release of hydrogen sulfide. These include methods which reduce the growth of the anaerobic bacteria or which chemically bind sulfides. However, these methods have drawbacks, such as high costs, implementation difficulties and safety concerns.

In particular, ferrous and ferric chloride (iron) and liquid caustic soda (sodium hydroxide, pH 13–14) are currently added to sewers to control sulfide generation and corrosion. The iron is added continuously to bind the sulfide as a nonsoluble iron sulfide precipitate.

Caustic soda is generally added semi-weekly to provide a thirty minute, high pH, shock dose to the anaerobic bacteria. The addition of caustic soda acts by neutralizing the sulfuric acid which has already been formed by the bacteria, inactivating and destroying the bacteria, and limiting the formation of new colonies of bacteria.

The use of caustic soda has been found to have several drawbacks. First, caustic soda only has a temporary effect on the bacteria. Second, caustic soda is hazardous and is highly toxic to humans. Even a small amount of caustic soda can cause permanent blindness.

It is expected that in the future the generation of hydrogen sulfide ($H_2S$) will increase, particularly as more municipalities adopt water conservation programs that include the installation of low-flow plumbing devices. As a result of the reduced flows in such systems, water may be retained longer in the pipes, wet wells and force mains of the collection system; damming caused by settled solids and grease may increase; and less dissolved oxygen (DO) may be present due to increased biochemical oxygen demand (BOD). Absent the teachings of the present invention, all of these changes might otherwise exacerbate the problems addressed by the invention.

SUMMARY OF THE INVENTION

It is therefore an object of the present invention to provide methods which are safe and effective for controlling the formation and release of acid gases, particularly hydrogen sulfide.

It is also an object of the present invention to provide a method of maintaining a level of hydrogen sulfide which is below an acceptable level.

It is a further object of the invention to provide methods of reducing or eliminating odor associated with waste water or sewerage.

It is also an object of the present invention to provide a method to minimize the formation and release of both hydrogen sulfide and ammonia in waste water or sewerage.

It has been found that the formation and release of acid gases, particularly hydrogen sulfide, which are associated with the unpleasant odor of sewerage and waste water can be controlled or eliminated by introducing magnesium hydroxide and/or magnesium oxide into the contaminated water. Moreover, it has surprisingly been shown that magnesium hydroxide is able to maintain a pH level which minimizes the levels of both hydrogen sulfide and ammonia. Further, the levels of hydrogen sulfide and the pH of the contaminated water can be maintained at an acceptable level for a significant period of time.

Other features and advantages of the present invention will become apparent from the following description of the invention which refers to the accompanying drawings.

BRIEF DESCRIPTION OF THE DRAWINGS

For the purpose of illustrating the invention, there is shown in the drawings an embodiment which is presently preferred; it being understood, however, that the invention is not limited by the precise arrangements and instrumentalities shown.

FIG. 3 is a diagram of a representative configuration for the addition of magnesium hydroxide and/or oxide to waste water or sewerage.

DETAILED DESCRIPTION OF THE INVENTION

It has been found that the addition of an agent including magnesium hydroxide ($Mg(OH)_2$), and/or magnesium oxide (MgO) to sewerage or waste water which is contaminated with compounds which can be reduced to acid gases, reduces or eliminates the release of these gases and the odor associated therewith.

The addition such an agent to sewerage or waste water is able to alter the pH of the solution into a preferred range of approximately 7.5 to 9.5, and to maintain pH in that preferred range for extended periods. The amount of the agent needed to achieve the preferred pH varies with the amount of water to be treated. Monitoring pH of the treated water during addition of the agent is recommended so that the operator may increase or decrease the amount of agent as necessary.

In general, the fraction of hydrogen sulfide relative to ionized hydrogen sulfide which is present in solution is dependent on the pH of the solution. It is desirable to reduce the level of hydrogen sulfide which is not ionized so as to reduce the unpleasant and harmful odors associated therewith. As discussed in more detail below, applicants have discovered that a pH of 7.5–9.5 (especially 8.0–9.0) is particularly preferred both for reducing release of acid gas and also for maintaining better levels of other compounds as well.

Figure 1:
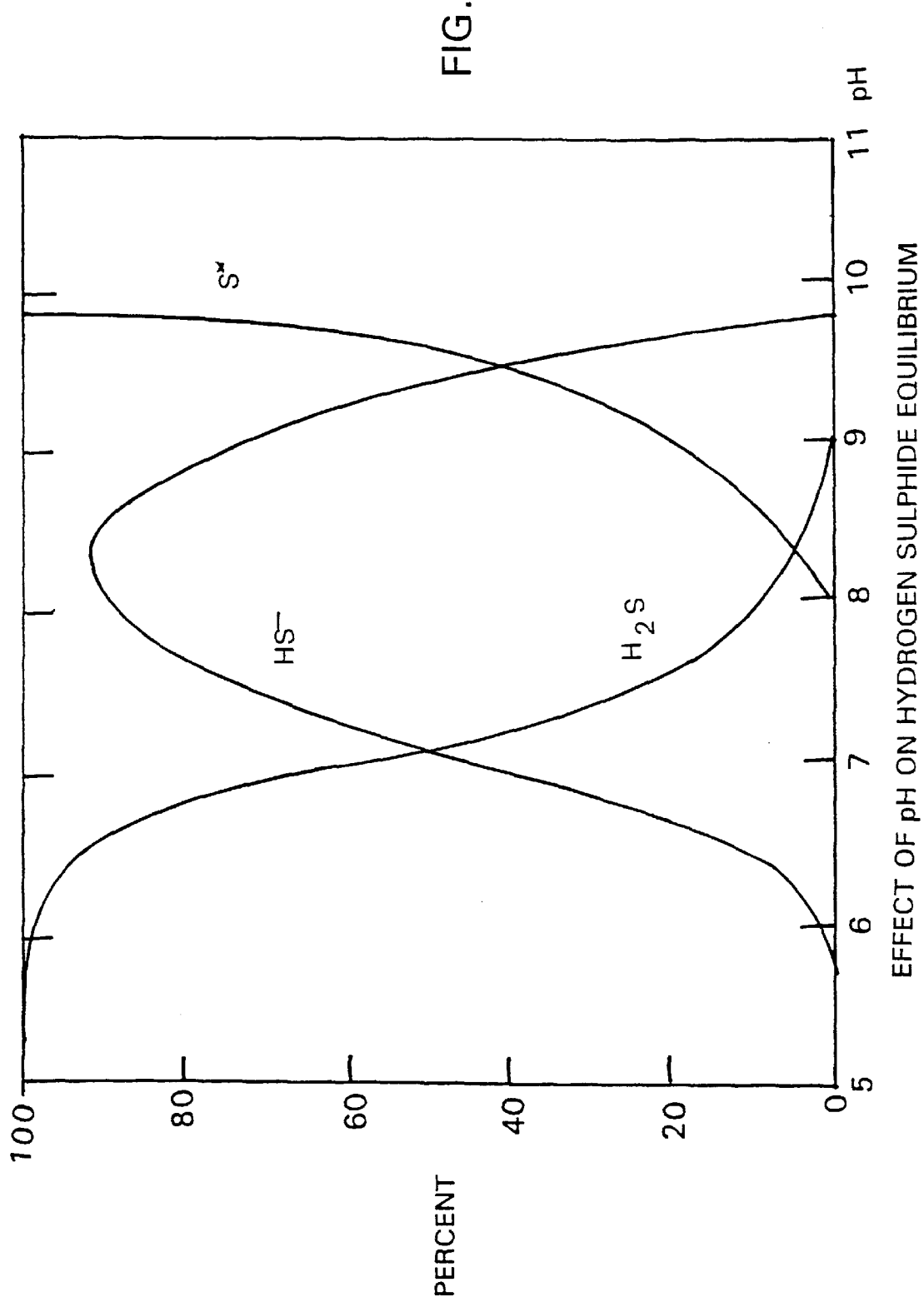
FIG. 1 is graph of the relative concentrations of hydrogen sulfide and ionized hydrogen sulfide at various pH levels.

As shown in FIG. 1, which compares the ratio of hydrogen sulfide to ionized hydrogen sulfide, at a constant temperature, the percentage of ionized hydrogen sulfide increases with an increase in pH. The largest effect is seen in the pH range of 6.0 to 8.0. In particular, at a pH of 6.0, 90.1% is hydrogen sulfide, while at a pH of 8.0, only 8.3% is hydrogen sulfide. Further, at a pH of 8.5, 3% is hydrogen sulfide and at a pH of 9.0, the hydrogen sulfide level drops to less than 1%.

Therefore, due to the relative insolubility of the agent of the invention, conditions can be maintained over time in which the amount of hydrogen sulfide which is present or released is reduced and therefore, the odors associated with the release or presence of hydrogen sulfide are minimized or eliminated. In some embodiments, hydrogen sulfide levels are desirably reduced to six parts per million or less.

Further, it has surprisingly been found that, at the preferred pH's of the invention, the undesirable release of ammonia is also minimized. In contrast to hydrogen sulfide levels, which decrease as the pH increases, the release of ammonia gas increases with an increase in pH. Therefore, a balance is preferred in which the pH level is both (1) high enough to reduce the formation and release of hydrogen sulfide and (2) low enough to prevent the formation and release of ammonia. It has been found that the optimal balance can be achieved by maintaining a pH in the range of approximately 7.5 to 9.5, especially 8.0 to 9.0, and most preferably, by maintaining a pH of approximately 8.3.

Moreover, a pH level substantially above 9.0 can be harmful to bacteria which are beneficial to treatment of waste water and sewerage. In comparison to other pH increasing compounds, magnesium hydroxide has been found to slowly reach and maintain a pH in the desired range without substantially overshooting the maximum level. As such, there is less osmotic shock and the helpful organisms are not destroyed.

Therefore, magnesium hydroxide and/or oxide have been found to be particularly suitable for the prevention of odor release in sewerage and waste water since the alkalinity and properties of magnesium hydroxide are such that it is easy for the operator to keep pH levels within the preferred range discussed above, without inadvertently raising pH so far above the preferred range that the undesirable effects discussed above become problematic.

Figure 2:
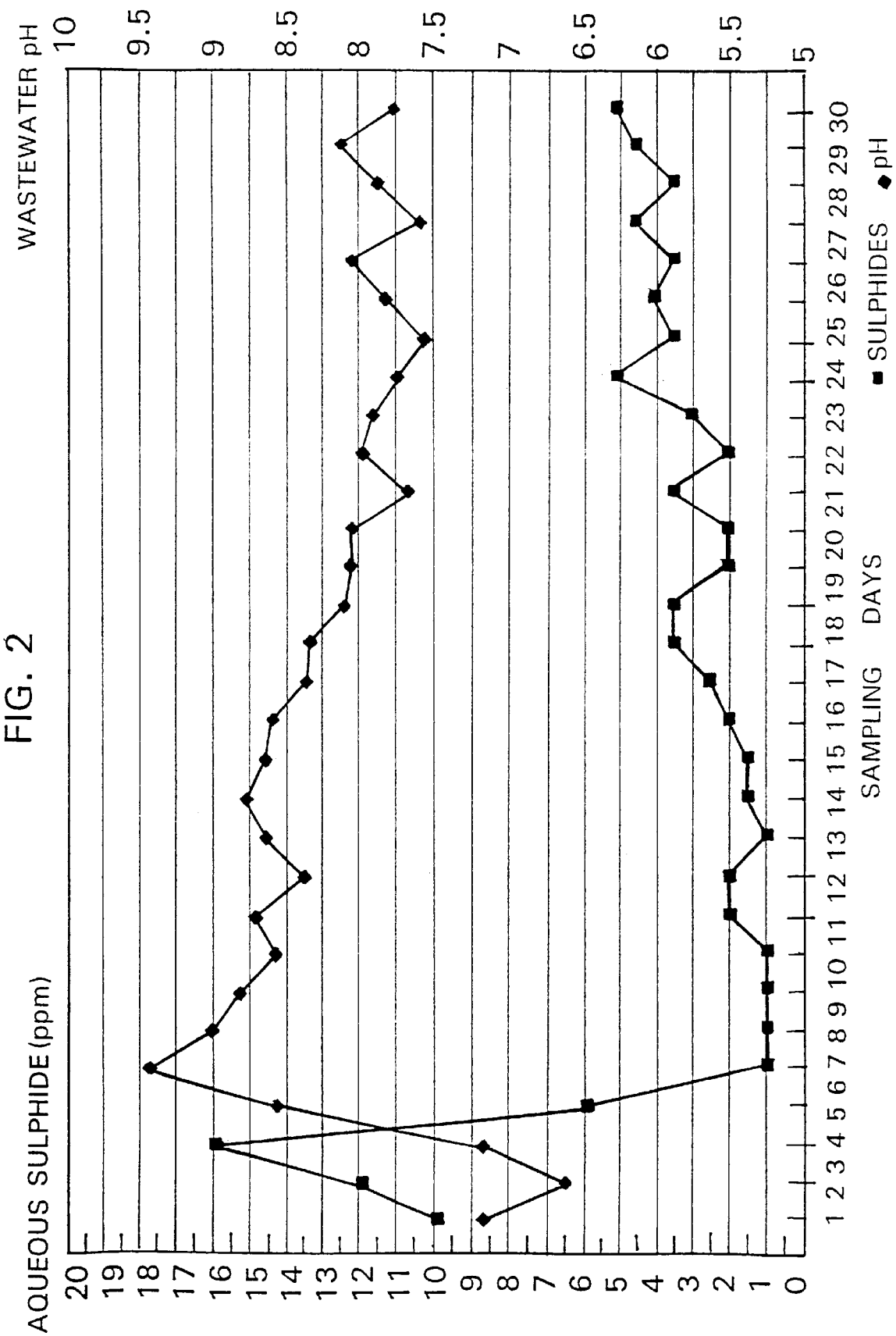
FIG. 2 is a graph of the pH level and aqueous sulfide level after the addition of magnesium hydroxide.

Moreover, it has been found that the low solubility of the magnesium leads to a time released alkalinity so that the pH level is more stable and is maintained upstream for a longer period of time. As shown in FIG. 2, magnesium hydroxide was able to maintain a pH of above 7.5 and a level of aqueous sulfides at or below 5 ppm for thirty days.

In addition to the benefits of magnesium hydroxide and/or oxide discussed above, the use of magnesium hydroxide and/or oxide is preferable for a number of reasons. First, it is noted that magnesium hydroxide requires no placarding or special handling and presents no chemical hazard to the environment, users, or the public. Second, magnesium hydroxide has a higher neutralizing capacity per mole than caustic soda due to its two OH ions. Third, the by-products produced by the reaction of magnesium with hydrogen sulfide tend not to be hazardous as with some by-products of hydrogen sulfide reactions. Finally, the magnesium requirements are less dependent on sulfide concentration.

It is believed that two mechanisms are responsible for the effectiveness of magnesium hydroxide and/or magnesium oxide. First, magnesium hydroxide has a pH of approximately 10.5, which, while safe to humans, is above the tolerance of common acid producing bacteria. It is noted that small amounts of lime (calcium hydroxide) can be added to magnesium hydroxide and/or magnesium oxide slurry to increase the pH and enhance the slurry's ability to kill bacteria. It is anticipated that other biocides or hardening agents such as sodium silicate, sodium bi-sulfate, magnesium sulfate, magnesium chloride, phosphates, or other materials intended to impart mechanical strength, may be added to further enhance its performance.

Secondly, as the bacteria is re-established, the alkalinity provided by the magnesium hydroxide and/or magnesium oxide neutralizes the acids produced by the bacteria and prevents the rapid re-establishment of bacteria.

A magnesium hydroxide and/or magnesium oxide slurry can be prepared by adding caustic calcined magnesium oxide (MgO), preferably in a dry powder form, to water. The magnesia can be obtained from any of the known suppliers including Premier Services Corporation, King of Prussia, Pa. Premier Services sells magnesia in dry powder form under the trademark MAGOX®.

When magnesium oxide is added to water it undergoes hydration and is converted to magnesium hydroxide. The rate of this reaction can be varied depending upon the surface area of the MgO, starting water temperature, vessel configuration, and agitation. Either a slowly hydrating MgO, or a fully hydrated $Mg(OH)_2$ slurry may be added to the contaminated water.

A magnesium hydroxide slurry can also be purchased from any of the known suppliers, including Premier Services which sells a magnesium hydroxide slurry under the trademark AQUAMAG®.

In a preferred embodiment of the invention, a specially hydrated and formulated slurry, marketed by Premier Services Corporation under the trademark THIOGUARD™, is added to sewerage or waste water. Without intending to be broad by theory, it is believed that this slurry offers a safe, economic alternative reagent for acid neutralization and water treatment and has been found to be particularly effective in controlling odors inter alia by achieving the pH and other effects discussed herein. It is believed to neutralize harmful sulfuric acid. It is an off-white slurry composed predominately of agglomerated magnesium hydroxide particles and is made from hydrated calcined natural magnesite or precipitated from sea water, bitterns, or brines. Table I, below, sets forth a representative chemical analysis of it on a loss free basis.

TABLE I

| Viscosity, centipoise | 800–6000, typically 3000 |
|---|---|
| % Solids | 55–65 |
| Specific Surface Area | Typically 10 $m^2g^{-1}$ |
| Chemical Analysis (Dry Basis), wt % | |
| MgO | 90–99 |
| CaO | 0.3–4.0 |
| $SiO_2$ | 0.3–4.0 |
| $R^2O_3$ | 0.1–2.0 |

The component $R_2O_3$ refers to natural impurities such as $Al_2O_3$ and $Fe_2O_3$ which are indigenous to ore bodies. Other insolubles besides (or in addition to) $SiO_2$, e.g. $MgCO_3$ and/or $CaCO_3$ may be included. The product THIOGUARD™ is made from natural ore and there are some natural variations in the percentages of various ingredients as shown inter alia in Table I.

In a preferred embodiment, as shown in FIG. 3, the magnesium hydroxide or magnesium oxide in the form of a slurry is topically applied to a stream of sewerage or waste water. In particular, a storage tank or drum 1 which holds magnesium hydroxide and/or magnesium oxide pumps the magnesium through a maintenance hole 2 to a sewerage flow 3. Odors from downstream maintenance holes 4 and corrosion on crowns and maintenance holes 5 are reduced or eliminated.

Addition of sufficient THIOGUARD™ to the sewerage to raise the pH to 9.0–9.5, which takes somewhere between 8.5–100 mg/l, dependent upon type of sewerage is sufficient to reduce odor and corrosion problems in sanitary sewers. This occurs because at this pH dissolved hydrogen sulphide gas is at a minimum and does not tend to escape into gaseous phase and contribute to odor and corrosion. For instance addition of THIOGUARD™ to sewerage at approximately 100 mg/l results in an almost instantaneous drop of aqueous sulphides from an initial 16 ppm to less than 1.0 ppm for a period of 4 days and a subsequent rise to between 6–6.5 for a period of 50 days.

Apart from its ability to alter sewerage pH to reduce dissolved hydrogen sulphide gas, there is a surface reaction between THIOGUARD™ and dissolved hydrogen sulphide, which results in adsorption of the gas onto the solids phase.

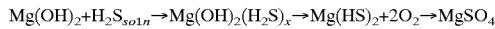

$$Mg(OH)_2 + H_2S_{soln} \to Mg(OH)_2(H_2S)_x \to Mg(HS)_2 + 2O_2 \to MgSO_4$$

Further reaction results in the formation of magnesium hydrosulphide, which can be oxidized by dissolved oxygen to form soluble magnesium sulphate which does not substantially contribute to odor or corrosion.

Due to its limited solubility in water, it is very slow to release hydroxyl ion (OH$^-$) in normal pH range of sewerage compared to other alkalis such as lime and caustic soda.

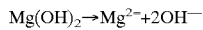

$$Mg(OH)_2 \to Mg^{2+} + 2OH^-$$

Consequently, THIOGUARD™ is able to continue to raise the pH downstream of the original point of addition without resulting in excessively high local pH's. For instance, adding it at a rate of 100 mg/l to sewerage is capable of sustaining a pH greater than 8.5 for 24 hours.

Its use to control odor/corrosion problems in sewerage is not limited to just hydrogen sulphide but could encompass other acidic gases/vapors such as sulphur dioxide and sulphur compounds which contain an ionizable hydrogen ion, such as mercaptans containing the —SH group.

It should be realized by those skilled in the art that the magnesium hydroxide and/or magnesium oxide can be added to any other water or liquid solution that is contaminated by compounds which can be reduced to acid gases, particularly sulfates and mercaptans.

The characteristics of the magnesium hydroxide and/or magnesium oxide slurry can be varied to provide the optimum pumping characteristics and to treat different levels of contamination.

The properties of the slurry can be varied by any of the known methods including changes in the solids to water ratio, or by the use of polymers to enhance or alter these properties as desired for differing field conditions or equipment configurations, e.g., increasing or decreasing the water content or by adding in more magnesia powder.

It is recommended that the slurry should include at least 30%, preferably at least 50%, by weight magnesium compound in the form of magnesium oxide, magnesium hydroxide or a mixture thereof.

Magnesium oxide can also be mixed with sodium silicate to produce a slurry which, when dried, yields a hard alkaline material composite of unhydrated magnesium oxide encapsulated in sodium silicate. In some embodiments, this dry form may constitute the agent added to sewerage or waste water in accordance with the invention. The acid produced by surface bacteria is neutralized by the sodium silicate. In addition, as the sodium silicate dissolves, the magnesium oxide is exposed, thereby dehydrating the bacteria and neutralizing the hydrogen sulfide.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

We claim:

1. A method for reducing the formation and release of hydrogen sulfide in municipal sewerage or waste water, comprising the step of:

adding an effective amount of an agent that includes a compound selected from the group consisting of magnesium hydroxide and magnesium oxide to said municipal sewerage or waste water, wherein said municipal sewerage or waste water includes at lease one compound which can be reduced to form hydrogen sulfide.

2. The method, as recited in claim 1, wherein said agent is a slurry further including sodium silicate.

3. The method, as recited in claim 1, wherein said agent is a hard alkaline material composite of unhydrated magnesium oxide encapsulated in sodium silicate.

4. The method, as recited in claim 1, wherein the composition is a slurry including:

| Chemical Analysis (loss free basis) | wt. % |
| --- | --- |
| MgO | about 92–98% |
| CaO | about .5–3.5% |
| R$^2$O$_3$ | about .5–1.5% |
| insolubles | about .5–3.0% |
| viscosity, cps | about 500–10,000 |
| density, lb/gal | about 11.2–11.8 |
| % solids by wt % | about 45–55 |

5. The method, as recited in claim 1, wherein said agent is substantially continuously added to said sewerage or waste water.

6. A method of controlling hydrogen sulfide odor associated with municipal sewerage or waste water, comprising the step of:

adding an effective amount of an agent that includes a compound selected from the group consisting of magnesium hydroxide and magnesium oxide to said municipal sewerage or waste water, wherein said municipal sewerage or waste water includes at least one compound which can be reduced to form hydrogen sulfide.

7. A method of obtaining a minimal level of hydrogen sulfide and of ammonia in municipal waste water or sewerage, comprising the step of:

adding an effective amount of an agent that includes a compound selected from the group consisting of magnesium hydroxide and magnesium oxide to said municipal sewerage or waste water, wherein said municipal sewerage or waste water includes at least one compound which can be reduced to form hydrogen sulfide.

8. The method of claim 1, wherein said agent is added in an amount effective to reduce hydrogen sulfide levels to no more than 6 parts per million.

9. The method of claim 6, wherein said agent is added in an amount effective to reduce hydrogen sulfide levels to no more than 6 parts per million.

10. The method of claim 7, wherein said agent is added in an amount effective to reduce hydrogen sulfide levels to no more than 6 parts per million.

11. The method of claim 1, wherein said agent is added in an amount effective to maintain pH of said sewerage or waste water between 7.5 and 9.5.

12. The method of claim 6, wherein said agent is added in an amount effective to maintain pH of said sewerage or waste water between about 7.5 and 9.5.

13. The method of claim 7, wherein said agent is added in an amount effective to maintain pH of said sewerage or waste water between about 7.5 and 9.5.

14. The method of claim 1, wherein said agent is added in an amount effective to maintain pH of said sewerage or waste water between about 8.0 and 9.0.

15. The method of claim 6, wherein said agent is added in an amount effective to maintain pH of said sewerage or waste water between about 8.0 and 9.0.

16. The method of claim 7, wherein said agent is added in an amount effective to maintain pH of said sewerage or waste water between about 8.0 and 9.0.

17. The method of claim 1, wherein said agent is added in an amount effective to maintain pH of about 8.3.

18. The method of claim 6, wherein said agent is added in an amount effective to maintain pH of about 8.3.

19. The method of claim 7, wherein said agent is added in an amount effective to maintain pH of about 8.3.

20. The method of claim 1, wherein lime is also added.

21. The method of claim 6, wherein lime is also added.

22. The method of claim 7, wherein lime is also added.

23. The method of claim 1, wherein said agent is a slurry comprising 30–50% by weight of said magnesium.

24. The method of claim 6, wherein said agent is a slurry comprising 30–50% by weight of said magnesium.

25. The method of claim 7, wherein said agent is a slurry comprising 30–50% by weight of said magnesium.

26. The method, as recited in claim 1, wherein the composition is a slurry including: Physical and Chemical Properties of THIOGUARD™ Chemical Analysis (Dry Basis), wt %

| | |
|---|---|
| MgO | about 90–99 |
| CaO | about 0.3–4.0 |
| $SiO_2$ | about 0.3–4.0 |
| $R^2O_3$ | about 0.1–2.0 |
| Viscosity | 800–6000 centipoise; |
| % Solids | about 55–65. |

* * * * *

UNITED STATES PATENT AND TRADEMARK OFFICE
CERTIFICATE OF CORRECTION

PATENT NO. : 5,833,864  
APPLICATION NO. : 08/680502  
DATED : November 10, 1998  
INVENTOR(S) : Thomas M. Miller et al.

Page 1 of 1

It is certified that error appears in the above-identified patent and that said Letters Patent is hereby corrected as shown below:

Claim 1, Column 6, line 21, "lease" should read --least--.

Claim 4, Column 6, line 36, "$R^2O_3$" should read --$R_2O_3$--.

Claim 26, Column 8, line 21, "$R^2O_3$" should read --$R_2O_3$--.

Signed and Sealed this

Twentieth Day of November, 2012

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 5,833,864 C1 |
| APPLICATION NO. | : 90/011643 |
| DATED | : April 14, 2011 |
| INVENTOR(S) | : Thomas M. Miller et al. |

Page 1 of 1

It is certified that error appears in the above-identified patent and that said Letters Patent is hereby corrected as shown below:

In the Claims:

Claim 32, Column 2, line 37, should read --amount of at least about 8.5.--

Signed and Sealed this
Eighteenth Day of June, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 5,833,864 C1  
APPLICATION NO. : 08/680502  
DATED : January 23, 2013  
INVENTOR(S) : Thomas M. Miller et al.

Page 1 of 1

It is certified that error appears in the above-identified patent and that said Letters Patent is hereby corrected as shown below:

On the Title Page:

Item (73) Assignee should read:  
Premier Magnesia, LLC

Signed and Sealed this  
Eighth Day of October, 2013

Teresa Stanek Rea  
*Deputy Director of the United States Patent and Trademark Office*

(12) EX PARTE REEXAMINATION CERTIFICATE (9485th)

United States Patent
Miller et al.

(10) Number: US 5,833,864 C1
(45) Certificate Issued: Jan. 23, 2013

(54) METHOD FOR THE REDUCTION AND CONTROL OF THE RELEASE OF GAS AND ODORS FROM SEWAGE AND WASTE WATER

(75) Inventors: Thomas M. Miller, Walnut, CA (US); Mark A. Shand, Findlay, OH (US)

(73) Assignee: Bank of America, Philadelphia, PA (US)

Reexamination Request:
No. 90/011,643, Apr. 14, 2011

Reexamination Certificate for:
Patent No.: 5,833,864
Issued: Nov. 10, 1998
Appl. No.: 08/680,502
Filed: Jul. 8, 1996

Certificate of Correction issued Nov. 20, 2012.

Related U.S. Application Data

(63) Continuation of application No. 08/386,735, filed on Feb. 10, 1995, now abandoned.

(51) Int. Cl.
*A01N 59/06* (2006.01)
*C04B 41/45* (2006.01)
*C04B 41/68* (2006.01)
*C04B 41/65* (2006.01)
*C04B 41/60* (2006.01)
*C04B 41/50* (2006.01)
*C02F 1/50* (2006.01)
*C02F 1/66* (2006.01)
*C02F 1/52* (2006.01)

(52) U.S. Cl. .......... 210/724; 210/749; 210/903; 210/916
(58) Field of Classification Search .................. 210/724
See application file for complete search history.

(56) References Cited

To view the complete listing of prior art documents cited during the proceeding for Reexamination Control Number 90/011,643, please refer to the USPTO's public Patent Application Information Retrieval (PAIR) system under the Display References tab.

*Primary Examiner* — E. Leigh McKane

(57) ABSTRACT

A method for reducing and controlling the formation and release of acid gases and odors associated therewith, particularly from hydrogen sulfide, in sewerage or waste water, wherein magnesium hydroxide and/or magnesium oxide are added to the sewerage or waste water.

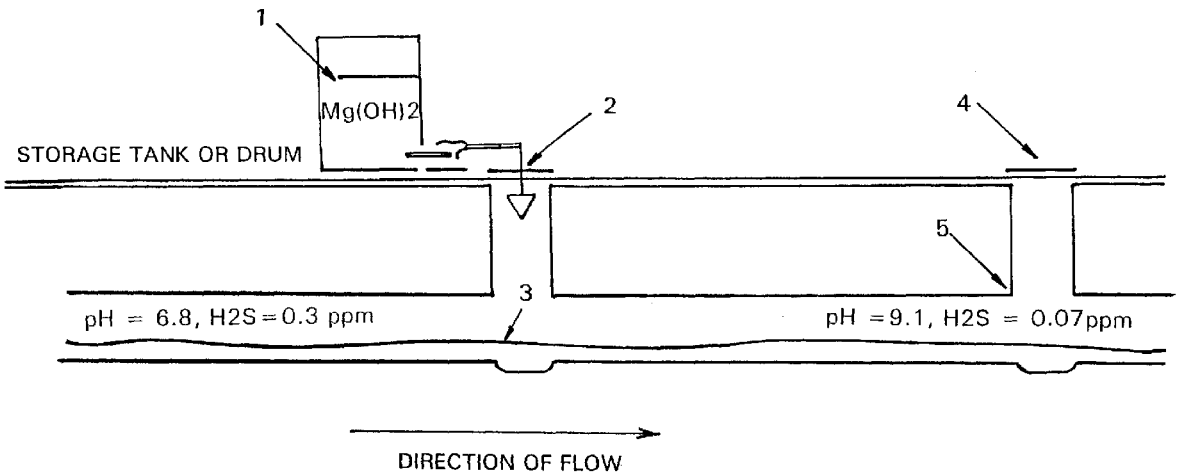

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 3, 4, 10, 13, 16, 19, 25 and 26 is confirmed.

Claims 1 and 7 are cancelled.

Claims 2, 5, 6, 8, 11, 14, 17, 20, 22 and 23 are determined to be patentable as amended.

Claims 9, 12, 15, 18, 21 and 24, dependent on an amended claim, are determined to be patentable.

New claims 27-59 are added and determined to be patentable.

2. The method, as recited in claim [1] *53*, wherein said agent is a slurry further including sodium silicate.

5. The method, as recited in claim [1] *53*, wherein said agent is substantially continuously added to said sewerage or waste water.

6. A method of controlling hydrogen sulfide odor associated with municipal sewerage or waste water, comprising the step of:

adding an *agent that includes an* effective amount of [an agent that includes] a compound selected from the group consisting of magnesium hydroxide and magnesium oxide to said municipal sewerage or waste water, wherein said municipal sewerage or waste water includes at least one compound which can be reduced to form hydrogen sulfide.

8. The method of claim [1] *53*, wherein said agent is added in an amount effective to reduce hydrogen sulfide levels to no more than 6 parts per million.

11. The method of claim [1] *53*, wherein said agent is added in an amount effective to maintain pH of said sewerage or waste water between 7.5 and 9.5.

14. The method of claim [1] *53*, wherein said agent is added in an amount effective to maintain pH of said sewerage or waste water between about 8.0 and 9.0.

17. The method of claim [1] *53*, wherein said agent is added in an amount effective to maintain pH of about 8.3.

20. The method of claim [1] *53*, wherein lime is also added.

22. The method of claim [7] *54*, wherein lime is also added.

23. The method of claim [1] *53*, wherein said agent is a slurry comprising 30-50% by weight of said magnesium.

*27. The method according to claim 53, wherein said agent is a hard alkaline material composite of unhydrated magnesium oxide encapsulated in sodium silicate.*

*28. The method, as recited in claim 53, wherein the agent consists essentially of a slurry including:*

| Chemical Analysis (loss free basis) | wt. % |
| --- | --- |
| MgO | about 92-98% |
| CaO | about .5-3.5% |
| $R_2O_3$ | about .5-1.5% |
| insolubles | about .5-3.0% |
| viscosity, cps | about 500-10,000 |
| density, lb/gal | about 11.2-11.8 |
| % solids by wt % | about 45-55. |

*29. The method as recited in claim 53, wherein the agent consists essentially of a slurry including:*

| Physical and Chemical Properties of THIOGUARD ™ | |
| --- | --- |
| Chemical Analysis (Dry Basis), | wt % |
| MgO | about 90-99% |
| CaO | about 0.3-4.0% |
| $SiO_2$ | about 0.3-4.0% |
| $R_2O_3$ | about 0.1-2.0% |
| Viscosity | 800-6000 centipoise; |
| % Solids | about 55-65. |

*30. The method, as recited in claim 53, wherein the effective amount of the compound also reduces the formation and release of ammonia in said municipal sewerage or wastewater.*

*31. The method, as recited in claim 53, wherein addition of the effective amount of the compound to said municipal sewerage or waste water obtains a pH of above 7.5 and a level of aqueous hydrogen sulfide at or below 5 ppm for thirty days in said municipal sewerage or waste water.*

*32. The method, as recited in claim 53, wherein the effective amount of the compound selected from the group consisting of magnesium hydroxide and magnesium oxide comprises an amount of at least about 8.5 and 100 mg/l.*

*33. The method, as recited in claim 53, wherein the effective amount of the compound selected from the group consisting of magnesium hydroxide and magnesium oxide comprises an amount of between about 8.5 and 100 mg/l.*

*34. A method for reducing the formation and release of hydrogen sulfide in municipal sewerage or waste water, comprising the step of:*

*adding an effective amount of at least one compound selected from the group consisting of magnesium hydroxide and magnesium oxide to said municipal sewerage or waste water, wherein said municipal sewerage or waste water includes at least one compound which can be reduced to form hydrogen sulfide.*

*35. The method according to claim 34, wherein the effective amount of the at least one compound is further effective to reduce release of ammonia in municipal sewerage or waste water.*

*36. The method according to claim 34, wherein the effective amount of the at least one compound comprises at least 8.5 mg/l of municipal sewerage or waste water.*

*37. The method according to claim 34, wherein the effective amount of the at least one compound is added to a collection system.*

*38. The method according to claim 34, wherein the effective amount is added in the form of a slurry having at least 30% by weight of the at least one compound selected from the group consisting of magnesium hydroxide and magnesium oxide.*

*39. A method of controlling hydrogen sulfide odor associated with municipal sewerage or wastewater, comprising the step of:* adding an effective amount of at least one compound selected from the group consisting of magnesium hydroxide and magnesium oxide to said municipal sewerage or waste water, wherein said municipal sewerage or waste water includes at least one compound which can be reduced to form hydrogen sulfide.

40. The method according to claim 39, wherein the effective amount of the at least one compound is further effective to control ammonia odor associated with municipal sewerage or waste water.

41. The method according to claim 39, wherein the effective amount of the at least one compound comprises at least 8.5 mg/l of municipal sewerage or waste water.

42. The method according to claim 39, wherein the effective amount of the at least one compound is added to a collection system.

43. The method according to claim 39, wherein the effective amount is added in the form of a slurry having at least 30% by weight of the at least one compound selected from the group consisting of magnesium hydroxide and magnesium oxide.

44. A method of obtaining a minimal level of hydrogen sulfide and of ammonia in municipal waste water or sewerage, comprising the step of:
adding an effective amount of at least one compound selected from the group consisting of magnesium hydroxide and magnesium oxide to said municipal sewerage or waste water, wherein said municipal sewerage or waste water includes at least one compound which can be reduced to form hydrogen sulfide.

45. A method for reducing the formation and release of hydrogen sulfide in municipal sewerage or wastewater in a municipal collection system, comprising the step of:
adding an agent that includes an effective amount of at least one compound selected from the group consisting of magnesium hydroxide and magnesium oxide to said municipal sewerage or waste water as contained in said municipal collection system, wherein said municipal sewerage or wastewater includes at least one compound that can be reduced to form hydrogen sulfide.

46. The method according to claim 45, wherein the agent includes a slurry having at least 30% by weight of the at least one compound selected from the group consisting of magnesium hydroxide and magnesium oxide.

47. The method according to claim 45, wherein addition of the effective amount of the at least one compound to said municipal sewerage or waste water obtains a pH of above about 7.5 and a level of aqueous hydrogen sulfide at or below 5 ppm for thirty days in said municipal sewerage or waste water in the municipal collection system.

48. A method of controlling hydrogen sulfide odor associated with sewerage or wastewater in a municipal collection system, comprising the step of:
adding an agent that includes an effective amount of a compound selected from the group consisting of magnesium hydroxide and magnesium oxide to said municipal sewerage or waste water in said municipal collection system, wherein said municipal sewerage or wastewater includes at least one compound that can be reduced to form hydrogen sulfide.

49. The method according to claim 48, wherein the agent includes a slurry having at least 30% by weight of the at least one compound selected from the group consisting of magnesium hydroxide and magnesium oxide.

50. The method according to claim 48, wherein addition of the effective amount of the at least one compound to said municipal sewerage or waste water obtains a pH of above about 7.5 and a level of aqueous hydrogen sulfide at or below 5 ppm for thirty days in said municipal sewerage or waste water in the municipal collection system.

51. A method of obtaining a minimal level of hydrogen sulfide and of ammonia in municipal sewerage or wastewater in a municipal collection system, comprising the step of:
adding an agent that includes an effective amount of a compound selected from the group consisting of magnesium hydroxide and magnesium oxide to said municipal sewerage or waste water in said municipal collection system, wherein said municipal sewerage or wastewater includes at least one compound that can be reduced to form hydrogen sulfide.

52. The method according to claim 51, wherein the effective amount of the compound comprises at least 8.5 mg/l magnesium oxide or magnesium hydroxide, which results in a pH of water in the municipal sewerage or waste water in said municipal collection system of between about 7.5 to 9.

53. A method for reducing the formation and release of hydrogen sulfide in municipal sewerage or waste water, comprising the step of:
adding an agent that includes an effective amount of a compound selected from the group consisting of magnesium hydroxide and magnesium oxide to said municipal sewerage or waste water, wherein said municipal sewerage or waste water includes at least one compound which can be reduced to form hydrogen sulfide.

54. A method of obtaining a minimal level of hydrogen sulfide and ammonia in municipal waste water or sewerage, comprising the step of:
adding an agent that includes an effective amount of a compound selected from the group consisting of magnesium hydroxide and magnesium oxide to said municipal sewerage or waste water, wherein said municipal sewerage or waste water includes at least one compound which can be reduced to form hydrogen sulfide.

55. The method of claim 54, wherein said agent is added in an amount effective to reduce hydrogen sulfide levels to no more than 6 parts per million.

56. The method of claim 54, wherein said agent is added in an amount effective maintain pH of said sewerage or waste water between about 7.5 and 9.5.

57. The method of claim 54, wherein said agent is added in an amount effective to maintain pH of said sewerage or waste water between about 8.0 and 9.0.

58. The method of claim 54, wherein said agent is added in amount effective to maintain pH of about 8.3.

59. The method of claim 54, wherein said agent is a slurry comprising 30-50% by weight of said magnesium.

* * * * *